United States Patent [19]

Shoesmith

[11] Plant 4,510

[45] Mar. 11, 1980

[54] CHRYSANTHEMUM NAMED ANTHEM

[75] Inventor: Leonard H. Shoesmith, Westfield-Woking, England

[73] Assignee: Pan-American Plant Company, West Chicago, Ill.

[21] Appl. No.: 955,147

[22] Filed: Oct. 26, 1978

[51] Int. Cl.[2] ..... A01H 5/00

[52] U.S. Cl. ..... Plt./74

[58] Field of Search ..... Plt./74

*Primary Examiner*—Robert E. Bagwill

*Attorney, Agent, or Firm*—Chas. W. Rummler

[57] ABSTRACT

A new cultivar of pot chrysanthemum characterized by its single flower form with several rows of medium pink ray florets which have very good substance and long life, its abundant production of blooms when grown as a spray pot, its minimal pollen production, and its ability for year around flowering on tall treatment.

4 Drawing Figures

BACKGROUND OF THE NEW PLANT

My new variety of pot chrysanthemum originated as a seedling of unknown parentage grown in greenhouse at West Chicago, Ill., from seeds of random pollinated greenhouse plants grown by me in 1971 at my breeding facilities in Westfield-Woking, Surrey, England. This plant was discovered and selected for propagation at West Chicago, Ill., in October 1972 in the course of a development program carried on under my direction for the production of new and improved chrysanthemum varieties for the commercial market.

This new plant was reproduced at West Chicago, Ill., by cuttings from the original plant and subsequent propagation of this new variety through successive generations has shown that not only does this plant have distinctive characteristics of commercial merit, but also that these characteristics hold true from generation to generation and appear to be firmly fixed.

At present, this new variety of pot chrysanthemum is propagated for commercial purposes, by vegetative cuttings, at West Chicago, Ill., and at Cortez, Fla.

DESCRIPTION OF THE DRAWINGS

My new variety of chrysanthemum is illustrated by the accompanying drawings; the first sheet of the drawings is a hand painted drawing showing face views of blooms to show their true colors; and the second sheet is a mechanical reproduction of photocopy prints of typical leaves of this variety illustrating their distinctive characteristics.

DESCRIPTION OF THE NEW PLANT

The following is a detailed description of my new chrysanthemum variety based upon observations of greenhouse plants grown at West Chicago, Ill., in 1977, the color designations being according to The R.H.S. Colour Chart published by The Royal Horticultural Society of London, England.

THE PLANT

Origin: Seedling.
Parentage: Unidentified.
Classification: Botanic — *Chrysanthemum morifolium.*
Form: Perennial herbaceous bush.
Height: About 32 to 40 cm.
Growth: Vigorous, upright and terminal, with very good strength and sturdiness.

Branching: Normal under natural conditions.
- Foliage: Quantity - Abundant with 7 to 9 leaves on about 10 cm. of stem.
  - *Leaf size.*—Length — about 6.5 to 14.1 cm. Width — about 3.4 to 9.4 cm.
  - *Leaf shape.*—Lobed, rather deeply cleft and slightly serrated.
  - *Surface aspect.*—Canescent.
  - *Color.*—Uper side — 137A. Under side — 146A.
  - *Venation.*—Pinnate.
  - *Petioles.*—Length — about 1.0 to 2.9 cm.

THE BUD

Form: Elliptical.
Size:
- *Diameter.*—About 12 to 14 mm.
- *Depth.*—About 7 to 9 mm.

Opening rate: Slow.
Color:
- *When phyllaries first divide.*—144A.
- *When florets begin to unfurl.*—58B.

Phyllaries: Many spear shaped and upstanding involucral bracts on the outside of the receptacle.
- *Color.*—Inside — 137C. Outside — 137C.
- *Surface aspect.*—Pubescent.

Peduncle: Character — sturdy and erect.
- *Length.*—2.3 to 7.4 cm.
- *Surface aspect.*—Pubescent.
- *Color.*—137C.

THE FLOWER

Recommended flowering: Year around with photoperiod control.
Response: 9 week.
Natural season flowering: October 20 to October 27.
Blooms:
- *Flower type.*—Composite and single.
- *Borne.*—As a head of many florets on a receptacle.
- *Size.*—Medium.
- *Diameter.*—6.2 to 7.3 cm.
- *Depth.*—11 to 18 mm.
- *Shape.*—Cup-shaped when bloom first opens, changing later to approach a flat shape.
- *Florets.*—Quantity — numerous. Form: — Linear with obtuse apex.

| Color: | April | June |
|---|---|---|
| Outer florets | 74D | 74C |
| Reverse side | 73D | 74D |

*Firmness.*—Firm.

*Appearance.*—Very slight shine.

Discoloration: Considerable fade after full bloom.

Persistence: Florets hang on and dry.

Fragrance: Typical chrysanthemum.

Lasting quality: On plant — 3 weeks. Not recommended for cut flower use.

REPRODUCTIVE ORGANS

Stamens: Number — 5.

*Arrangement.*—Syngenesious.

*Filaments.*—Length — about 2 to 5 mm.

*Color.*—Light yellow.

*Pollen.*—Color — yellow.

Pistils: Number - one to each ray and disc floret.

*Styles.*—About 5 to 6 mm. long.

*Stigmas.*—Color — yellow.

*Ovaries.*—Inferior bicarpellate.

This new variety of chrysanthemum is particularly characterized by its medium pink ray florets, of which there are several rows in a single form of bloom. The ray florets are of very good substance and have long life and the blooms, which have minimal pollen, are abundantly produced when grown as a spray pot plant.

This variety is also characterized by its relatively upright pot habit with strong stems and good breaking ability, with 4 to 6 breaks when manually pinched. This variety is not temperature sensitive and can be flowered year around on tall treatment, flowering 9 weeks after beginning of short days.

I claim:

1. A new and distinctive cultivar of pot chrysanthemum, substantially as herein shown and described, characterized by its single flower form with several rows of medium pink ray florets, and its abundant production of blooms having minimal pollen when grown as a spray pot plant, and by its relatively upright pot habit with strong stems and good breaking ability.

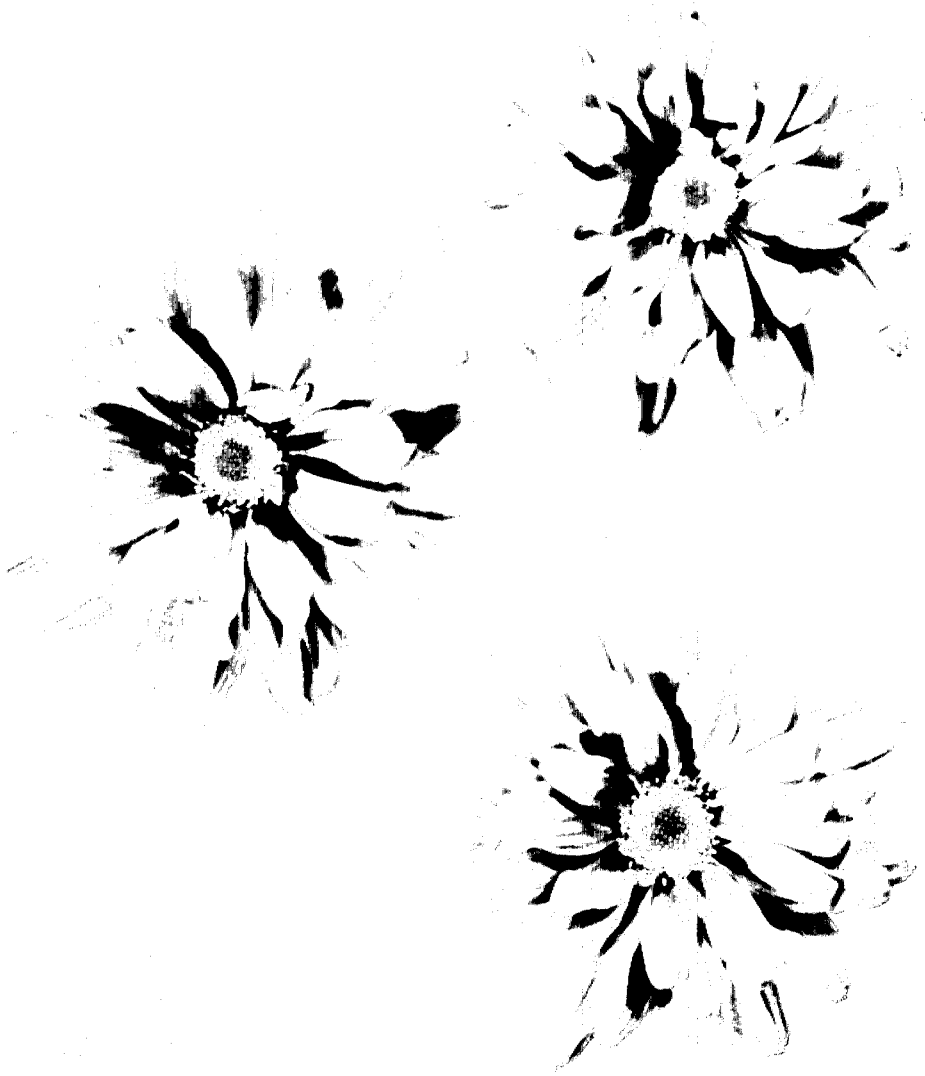

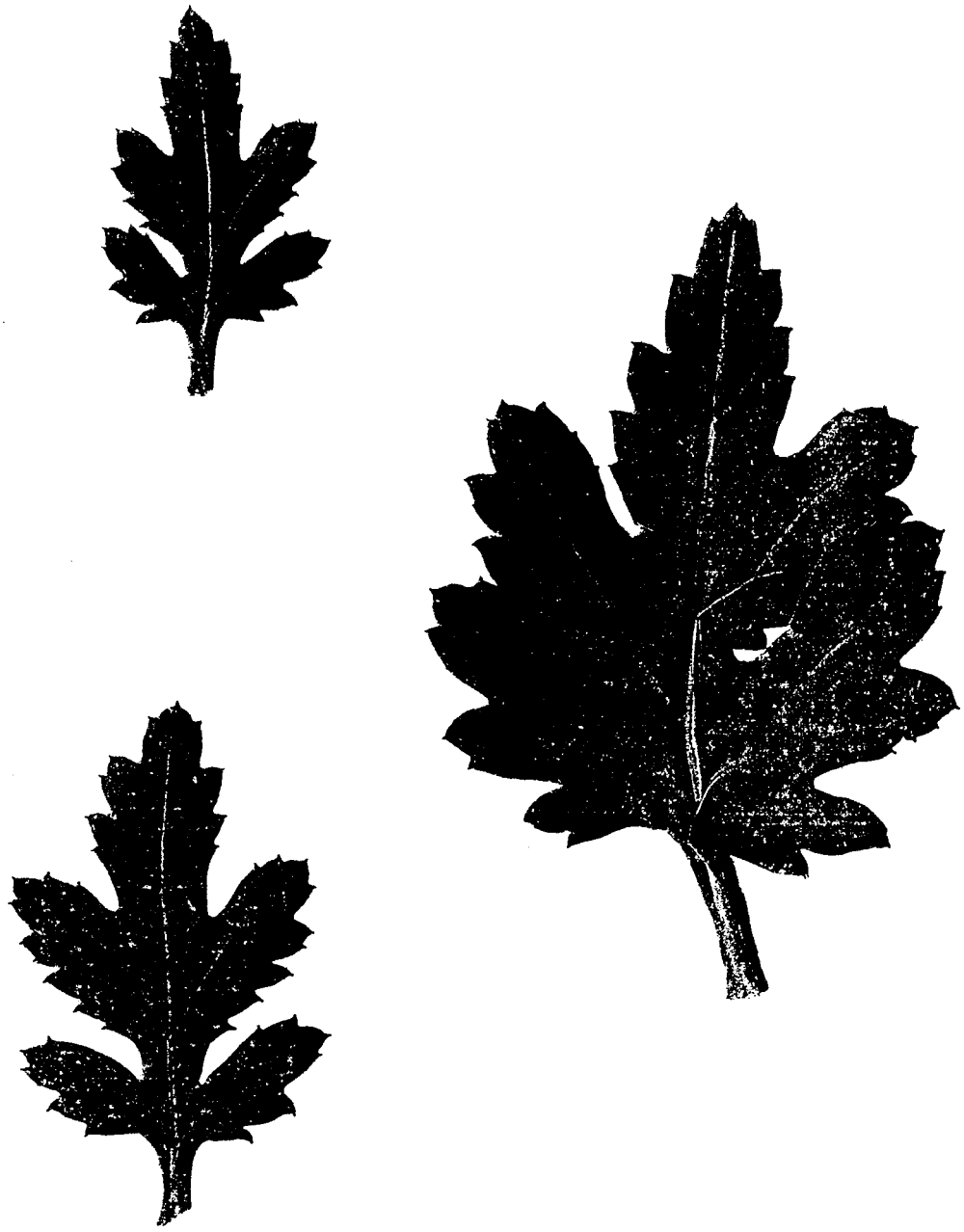

* * * * *